United States Patent
Baumgart (10) Patent No.: US 10,083,511 B2
(45) Date of Patent: Sep. 25, 2018

(54) ANGIOGRAPHIC ROADMAPPING MASK

(71) Applicant: Siemens Medical Solutions USA, Inc., Malvern, PA (US)

(72) Inventor: John Baumgart, Hoffman Estates, IL (US)

(73) Assignee: Siemens Healthcare GmbH, Erlangen (DE)

( * ) Notice: Subject to any disclaimer, the term of this patent is extended or adjusted under 35 U.S.C. 154(b) by 57 days.

(21) Appl. No.: 15/264,445

(22) Filed: Sep. 13, 2016

(65) Prior Publication Data

US 2017/0124708 A1 May 4, 2017

Related U.S. Application Data

(60) Provisional application No. 62/248,751, filed on Oct. 30, 2015.

(51) Int. Cl.
*G06K 9/00* (2006.01)
*G06T 7/00* (2017.01)

(52) U.S. Cl.
CPC .................. *G06T 7/0038* (2013.01)

(58) Field of Classification Search
None
See application file for complete search history.

(56) References Cited

U.S. PATENT DOCUMENTS

2009/0192385 A1* 7/2009 Meissner ............... A61B 6/032
600/426

* cited by examiner

*Primary Examiner* — Atiba O Fitzpatrick (57) ABSTRACT

Systems and methods are provided for angiographic roadmapping. In accordance with one aspect, the framework generates one or more two-dimensional (2D) digitally reconstructed radiograph (DRR) images from a four-dimensional (4D) digital subtraction angiography (DSA) image volume. A maximally opacified image is generated from at least one of the one or more 2D DRR images over a window of time. The maximally opacified image may then be integrated with a live fluoroscopic image and displayed for angiographic roadmapping.

21 Claims, 5 Drawing Sheets

ANGIOGRAPHIC ROADMAPPING MASK

CROSS-REFERENCE TO RELATED APPLICATION

The present application claims the benefit of U.S. provisional application No. 62/248,751 filed Oct. 30, 2015, the entire contents of which are herein incorporated by reference.

TECHNICAL FIELD

The present disclosure generally relates to image data processing, and more particularly to angiographic roadmapping masks.

BACKGROUND

Angiography is a common method used to represent blood vessels based on diagnostic imaging methods, such as X-ray or Magnetic Resonance Tomography (MRT). For an improved representation of vessels under examination, Digital Subtraction Angiography (DSA) has been developed. DSA is a fluoroscopy technique used in interventional radiology to clearly visualize blood vessels in a bony or dense soft tissue environment. Images are produced by subtracting a 'pre-contrast image' or the mask from subsequent images acquired after the contrast medium has been introduced into a structure or tissue of interest. These images can be used to provide time-resolved or time-varying information that shows the development of the structure or tissue of interest over time.

SUMMARY

Described herein are systems and methods for angiographic roadmapping. In accordance with one aspect, the framework generates one or more two-dimensional (2D) digitally reconstructed radiograph (DRR) images from a four-dimensional (4D) digital subtraction angiography (DSA) image volume. A maximally opacified image is generated from at least one of the one or more 2D DRR images over a window of time. The maximally opacified image may then be integrated with a live fluoroscopic image and displayed for angiographic roadmapping.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MM, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, doxels for 4D datasets). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture, 3D volume or 4D dataset. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image is itself synthesized from image data obtained as pixels on a 2D sensor array and displays as a 2D image from some angle of view. Thus, 2D image processing and image analysis techniques can be applied to the 3D volume image data. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

Angiographic roadmapping is a superimposition of a live fluoroscopic image on a previously stored digitally subtracted angiogram. This special type of image serves as a visual roadmap of blood vessels for doctors, interventional radiologists, and other users of the angiographic platform. Current two-dimensional (2D) angiographic roadmapping techniques use a contrast-filled frame from a previous acquisition as a mask to be registered with live fluoroscopic images to permit devices to be guided through vasculature without further injection of contrast media. Since the mask is taken at a fixed location and projection angle, any movement of the patient or change in the projection angle will necessitate the acquisition of a new mask frame, thus exposing the patient to both additional X-ray and contrast agent.

Three-dimensional (3D) angiographic roadmapping techniques typically overlay a static (e.g., non-time-varying) representation of the 3D anatomy, projected onto the 2D fluoroscopic image, using a previously acquired image volume. While these techniques provide the ability to adjust to changing the patient position or projection angle, the 3D roadmap does not contain flow information that can be used to select the anatomy of interest for a roadmap mask.

One aspect of the present framework facilitates the generation of a roadmapping mask. The roadmapping mask may be used for 2D angiographic roadmapping that incorporates additional information for selection of anatomy, while maintaining reduced exposure of X-ray and contrast agent to the patient. The roadmapping mask has characteristics of a 2D DSA frame with contrast present. In some implementations, the roadmapping mask is generated from a four-dimensional (4D) Digital Subtraction Angiography (DSA) image volume. The 4D DSA image volume is a time-varying 3D volume that contains additional flow information about the flow of contrast through vasculature over a period of time. As there is flow information present in the 4D DSA image volume, it is possible to select a time window as desired over which the contrast presence is captured for generating the roadmapping mask.

Advantageously, the roadmapping mask may easily be updated in response to, for example, movement or change in patient position and/or projection angle, without exposing the patient to further radiation or contrast agent. Additionally, such roadmapping mask generation enhances efficiency by reducing the total procedure time. These and other features and advantages will be described in more details herein. It is understood that while a particular application directed to vascular network visualization may be shown, the technology is not limited to the specific implementations illustrated.

Figure 1:
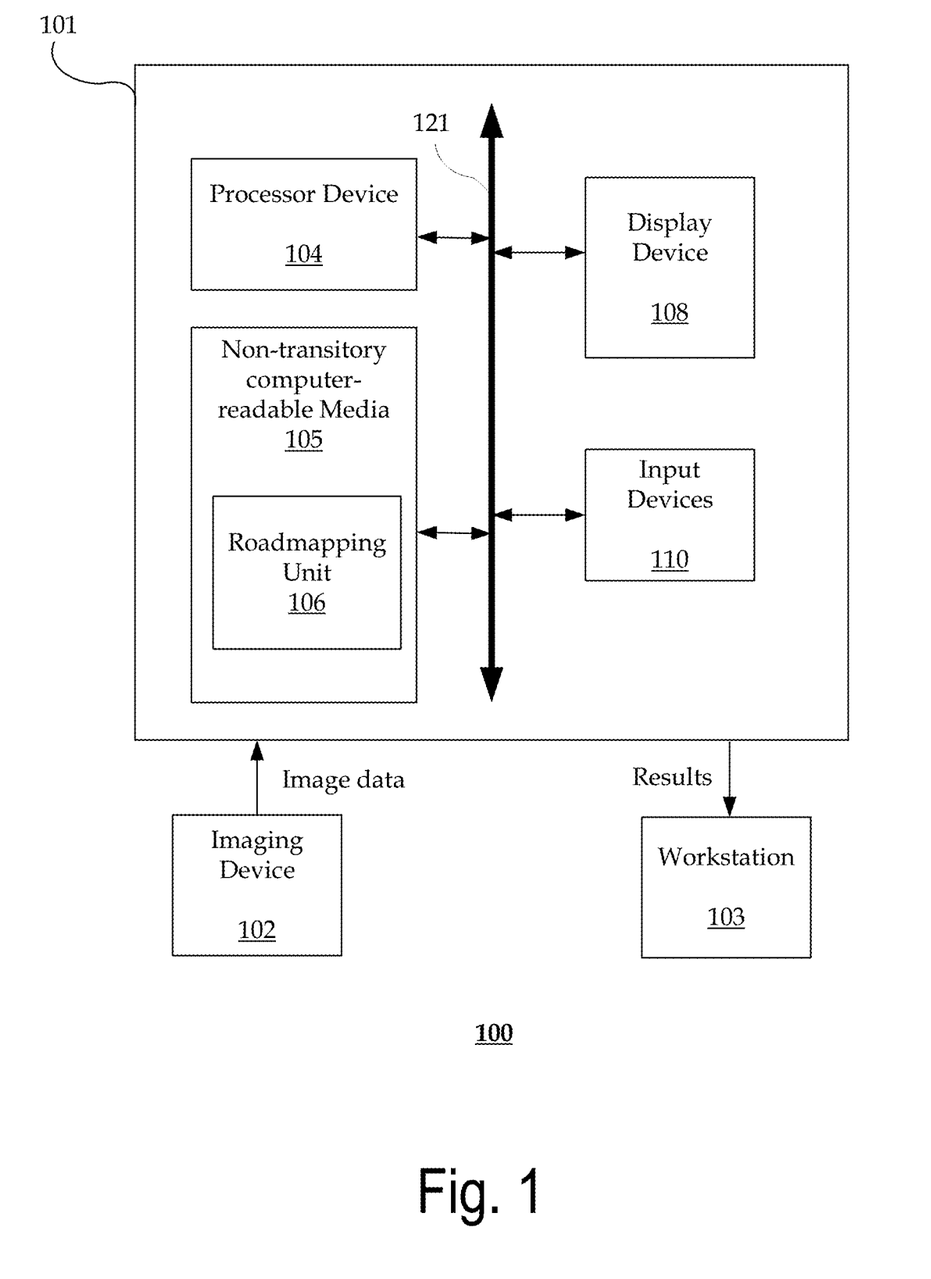
FIG. 1 is a block diagram illustrating an exemplary system.

FIG. 1 is a block diagram illustrating an exemplary system 100. The system 100 includes a computer system 101 for implementing the framework as described herein. Computer system 101 may be a desktop personal computer, a portable laptop computer, another portable device, a minicomputer, a mainframe computer, a server, a cloud infrastructure, a storage system, a dedicated digital appliance, a communication device, or another device having a storage sub-system configured to store a collection of digital data items. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server, such as Syngo®.via by Siemens Healthcare), a client user machine in server-client user network environment, or as a peer machine in a peer-to-peer (or distributed) network environment.

Computer system 101 may include a processor device or central processing unit (CPU) 104 coupled to one or more non-transitory computer-readable media 105 (e.g., computer storage or memory), display device 108 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a roadmapping unit 106. Non-transitory computer-readable media 105 may include random access memory (RAM), read-only memory (ROM), magnetic floppy disk, flash memory, and other types of memories, or a combination thereof. The computer-readable program code is executed by processor device 104 to process images or image data acquired by, for example, imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image datasets, knowledge base, and so forth. Such data may also be stored in external storage or other memories. The external storage may be implemented using a database management system (DBMS) managed by the processor device 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The imaging device 102 may be a radiology scanner, such as an X-ray or a CT scanner, for acquiring image data. The workstation 103 may include a computer and appropriate peripherals, such as a keyboard and display device, and can be operated in conjunction with the entire system 100. For example, the workstation 103 may communicate with the imaging device 102 so that the image data collected by the imaging device 102 can be rendered at the workstation 103 and viewed on a display device.

The workstation 103 may communicate directly with the computer system 101 to display processed image data and/or output image processing results (e.g., angiographic roadmapping mask). The workstation 103 may include a graphical user interface to receive user input via an input device (e.g., keyboard, mouse, touch screen, voice or video recognition interface, etc.) to manipulate visualization and/or processing of the image data. For example, the user may view the processed image data, and specify one or more view adjustments or preferences (e.g., desired time interval, zooming, cropping, panning, rotating, changing contrast, changing color, changing view angle, changing view depth, changing rendering or reconstruction technique, etc.), navigate to a particular region of interest by specifying a "goto" location, navigate (e.g., stop, play, step through, etc.) temporal volumes of an image dataset, and so forth.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
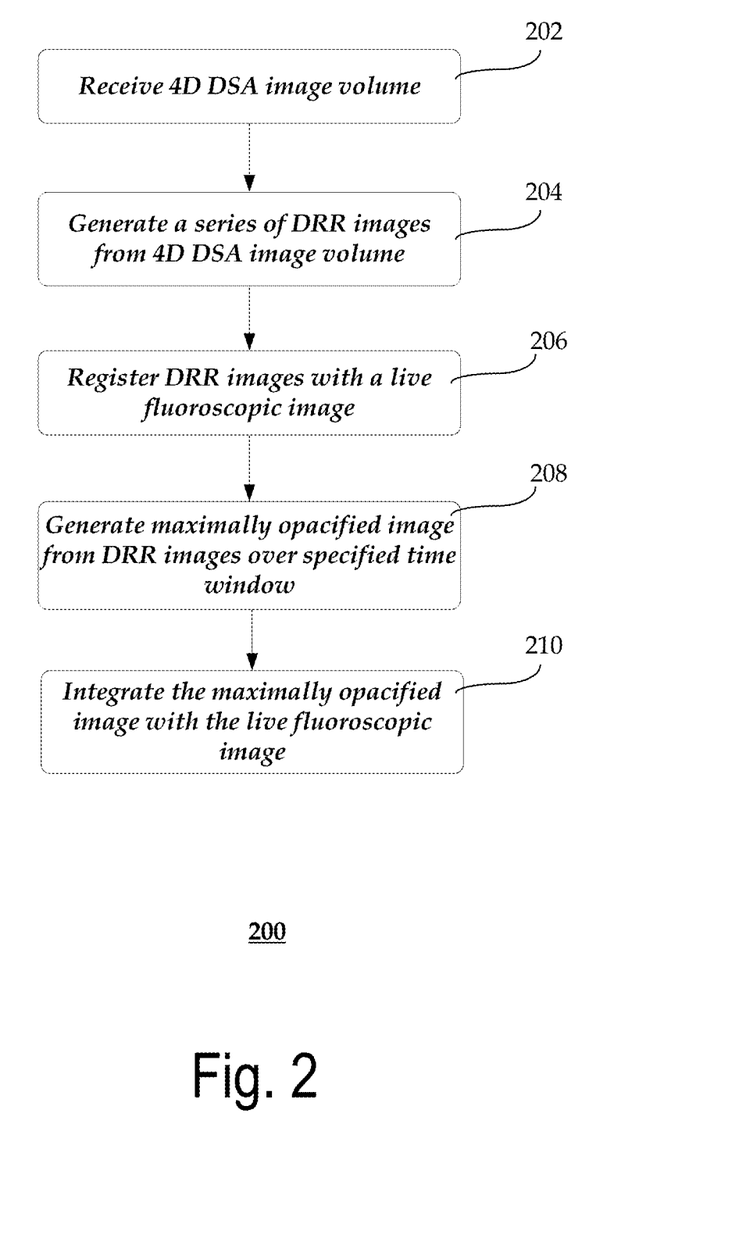
FIG. 2 shows an exemplary method of generating an angiographic roadmapping mask performed by a computer system.

FIG. 2 shows an exemplary method 200 of generating an angiographic roadmapping mask performed by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 202, roadmapping unit 106 receives a 4D DSA image volume. The 4D-DSA image volume may be generated by performing a 4D reconstruction of time-varying image data to generate a 4D DSA projection image dataset of an object of interest. Each doxel of the 4D DSA projection image dataset represents the injected contrast flow in the vasculature of the object of interest at a particular three-dimensional location and at a particular time. The object of interest may be any biological object identified for investigation or examination, such as a portion of a patient's or subject's brain, heart, leg, arm, and so forth. The object of interest includes one or more vessel-like structures (e.g., blood vessels, arteries, vascular tree or network, etc.). The one or more vessel-like structures may be dynamic or time-varying structures that can be filled with a contrast agent or medium for observing its propagation over time.

Figure 3A:
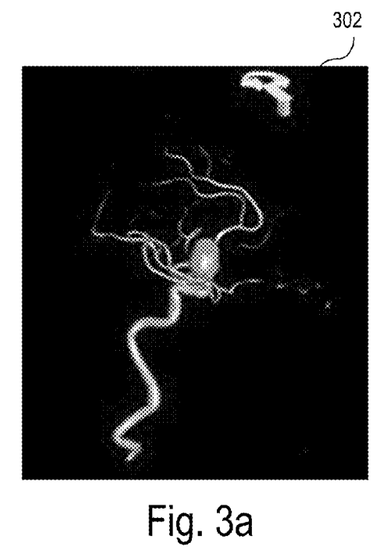
FIG. 3a illustrates an exemplary 4D DSA image volume of vasculature at a particular time.
Figure 3B:
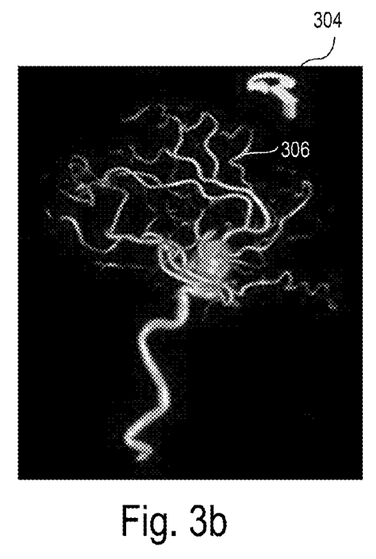
FIG. 3b shows an exemplary 4D DSA image volume of the same vasculature at a later time.

FIG. 3a illustrates an exemplary 4D DSA image volume 302 of vasculature at a particular time, while FIG. 3b shows an exemplary 4D DSA image volume 304 of the same vasculature at a later time. As shown in FIG. 3b, the flow of contrast has traveled even further into the vessel extremities 306. The 4D DSA image volumes (302, 304) may be generated by one or more image processor(s) based on time-varying data.

The time-varying data may be a set of 2D DSA projection images that are acquired by performing a rotational scan or angular acquisitions. A single mask and fill acquisition may be performed. More particularly, a mask image dataset may first be acquired such that it can be subtracted from the corresponding time-varying contrast filled projection image dataset. A mask image is simply an image of the same area before the contrast agent (or medium) is administered to fill the vessel-like structures of the irradiated object of interest that is to be investigated. The actual angular- and time-varying 2D projection data may be based on a contrast-enhanced acquisition that is initiated before or after the injection of X-ray contrast medium into the vessel-like structures as the first inflow of contrast becomes visible. Both mask and fill runs may follow the same acquisition trajectory. The trajectory may cover the entire field-of-view (FOV) range of a 3D DSA.

A scanner or C-arm system with a single imaging plane or multiple imaging planes may be used to acquire the 2D DSA projection images. Methods for performing a 4D-DSA reconstruction of time-varying image data acquired by a single rotating plane C-arm system are described in application Ser. No. 14/302,596 filed on Jun. 12, 2014 (now U.S. Pub. No. 2014/0376791), which is hereby incorporated by reference. These methods may determine time-varying volumetric attenuation curves of the vessel-like structures of interest, resulting in a 3D plus time (or 4D-DSA) volumetric dataset that includes the time dimension. The 4D-DSA image dataset may also be derived from time- and projection angle-varying data. Confidence values or curves may be used in performing interpolation of time-resolved 3D DSA. Such framework may be applied once, or in an iterative fashion. The 4D-DSA image dataset may also be dynamically and iteratively reconstructed based on, for example, an initial time-varying 3D projection dataset derived from time-varying 2D projection data acquired at multiple angles.

Methods for performing a 4D-DSA reconstruction of time-varying image data acquired by a dual C-arm system are described in German application no. 102015224176.9 filed on Dec. 3, 2015 entitled "Tomography system and method for generating a sequence of volume images of a vasculature" (also PCT application no. PCT/EP2015/079102 filed on Dec. 9, 2015), which are hereby incorporated by reference. These techniques are based on an angiographic biplane system that comprises two simultaneously rotating planes. The accuracy of the reconstructed series of time-resolved volumes can be significantly improved, since information from the two planes can be exploited to mitigate accuracy issues due to vascular overlap.

Referring to FIG. 2, at 204, roadmapping unit 106 generates a series of one or more digitally reconstructed radiograph (DRR) images from the 4D DSA image volume. A DRR image is a simulation of a conventional 2D X-ray image and is generated by projecting the 4D DSA image volume at a predetermined angle. A series of DRR frames for different time points may be generated at a predetermined angle substantially equal to the projection angle used to acquire a live (or current) 2D fluoroscopic (or X-ray) image. The live fluoroscopic image is a real-time X-ray image of the object of interest acquired by, for example, imaging device 102 during a medical intervention. The live fluoroscopic image is used for roadmapping, as will be described with reference to step 210.

Figure 3C:
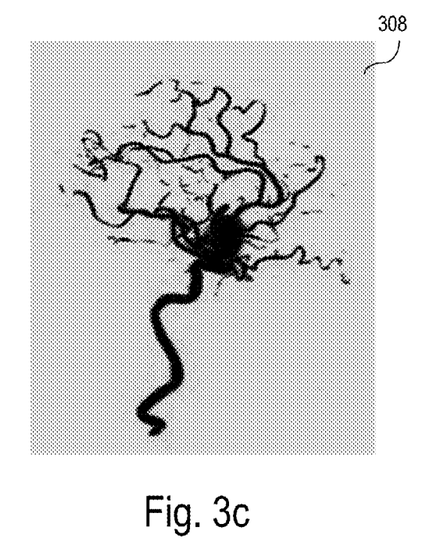
FIG. 3c shows an exemplary 2D DRR image.

Each frame in the series of DRR images shows contrast flow in the same volume at a particular time point. The series of DRR frames is roughly equivalent to a 2D DSA showing the flow of contrast into and out of the vessels of interest over various time points. FIG. 3c shows an exemplary 2D DRR image 308 generated from the 4D DSA image volumes 302 and 304 shown in FIGS. 3a and 3b. The 2D DRR image 308 resulted from the projections of 4D DSA image volumes 302 and 304, as combined by roadmapping unit 106.

Figure 4A:
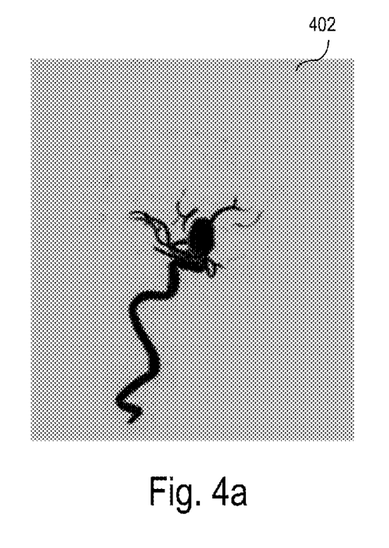
FIG. 4a illustrates a 2D DRR image at a particular point in time.
Figure 4B:
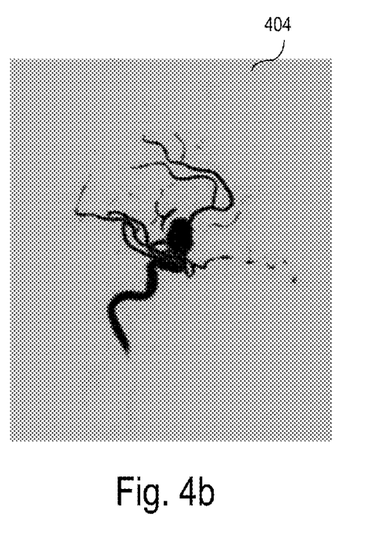
FIG. 4b illustrates a 2D DRR image based on the same volume but with contrast flow shown at a later time point.
Figure 4C:
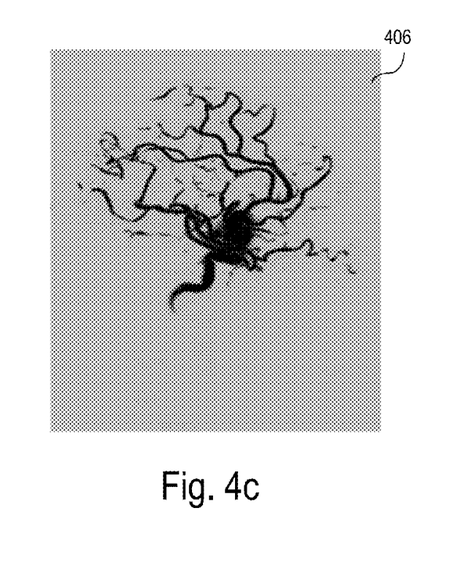
FIG. 4c illustrates a subsequent 2D DRR image based on the same 4D DSA image volume but with contrast flow shown at a later time point.

Roadmapping unit 106 may generate additional DRR images from the 4D DSA volume at different time points within a time period. FIGS. 4a, 4b and 4c show additional exemplary 2D DRR images. More particularly, FIG. 4a shows a 2D DRR image 402 at a particular point in time. FIG. 4b shows a 2D DRR image 404 based on the same 4D DSA image volume but with contrast flow shown at a later time point than that in the image 402. FIG. 4c illustrates a subsequent 2D DRR image 406 based on the same image volume but with contrast flow shown at a later time point than the image 404. The 2D DRR images 402, 404 and 406 represent frames, with each frame capturing the contrast flow at a particular point within a time period. In a series, images 402, 404 and 406 illustrate the contrast flow through the volume of vessels within a time period.

At 206, roadmapping unit 106 registers the DRR images with the live fluoroscopic image. Registration generally brings the DRR images and the live fluoroscopic image into the same coordinate frame. The registration may be performed by using a 2D to 2D (2D/2D) registration technique. Such 2D/2D registration may be rigid or deformable. The DRR images are shifted to match an optimal registration with the live fluoroscopic image.

At 208, roadmapping unit 106 generates a maximally opacified image using the DRR images over a specified time window. The maximally opacified image may serve as a roadmapping mask in the same manner as a 2D DSA image. Each pixel in the maximally opacified image represents the peak (or maximum) contrast intensity level at a particular location captured within the specified time window. To generate the maximally opacified image, the DRR images may be processed pixel by pixel to determine the peak (or maximum) contrast intensity level at each pixel location over the time window.

Figure 5:
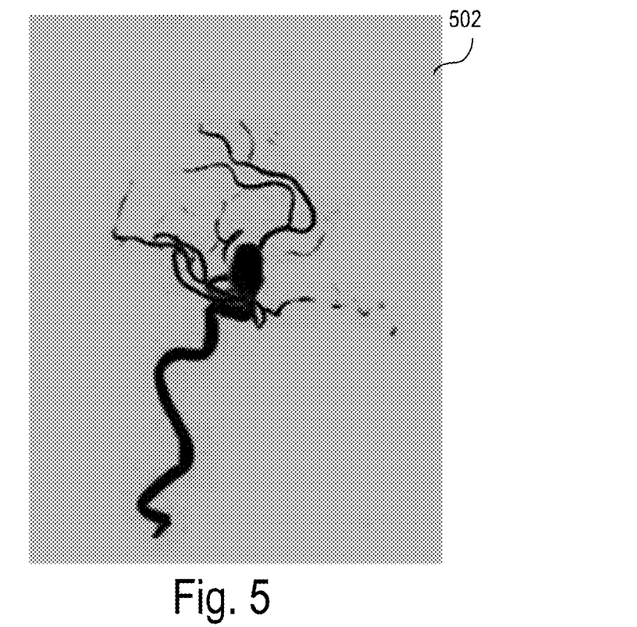
FIG. 5 shows an exemplary maximally opacified frame.

FIG. 5 shows an exemplary maximally opacified frame 502 generated from the 2D DRR image 402 and 404 shown in FIGS. 4a and 4b. In some implementations, roadmapping unit 106 generates a user interface (e.g., graphical user interface) that is configured to enable a user to specify a beginning time point and an end time point of the time window. The user interface may be accessed at, for example, workstation 103. The time window is smaller or equal to the time period captured by the entire series of DRR images. The DRR images corresponding to the specified time window are used to generate the maximally opacified image. The resultant maximally opacified image displays the contrast agent at its peak contrast level in each pixel location in the vessel volume where the contrast agent was present during the time window.

Returning to FIG. 2, at 210, roadmapping unit 106 integrates the maximally opacified frame with the live (or current) fluoroscopic image to generate a roadmapping fluoroscopic image. The maximally opacified frame may be integrated by subtracting it from the fluoroscopic image, which produces the effect of making the vessel regions with contrast bright on the resulting image. This enables the physician to see the catheter or guide wire being advanced through the vessels. It should be appreciated that other methods of integration may also be used.

Figure 6:
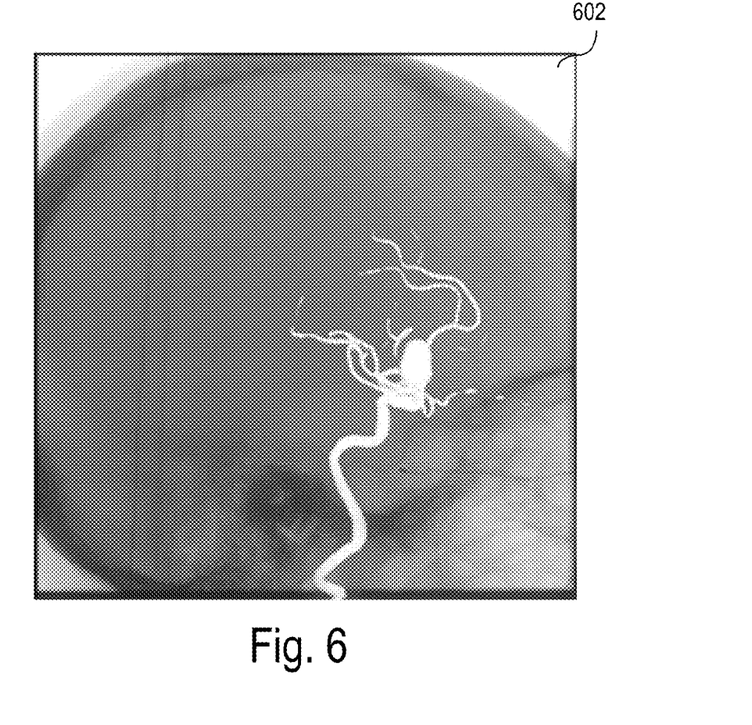
FIG. 6 shows an exemplary roadmapping fluoroscopic image.

FIG. 6 shows an exemplary roadmapping fluoroscopic image 602 generated by using the maximally opacified mask image 502 (as shown in FIG. 5) as the roadmapping mask. The maximally opacified image 502 is integrated with the live fluoroscopic image. The roadmapping fluoroscopic image 602 may be displayed at workstation 103. Workstation 103 may be, for example, a handheld mobile computing device (e.g., smartphone, tablet, laptop) or a monitor mounted to a wall or located near the patient table.

In some implementations, roadmapping unit 106 generates a user interface (e.g., graphical user interface) that is configured to enable a user to specify a projection angle of fluoroscopy or position of the patient (e.g., patient table position). Alternatively, the fluoroscopic projection angle or position of the patient may be automatically tracked (or detected) by, for example, determining the angulation of the C-arm or the position of the patient table. The user interface may be accessed at, for example, workstation 103. In response to a change in the fluoroscopic projection angle or patient position, roadmapping unit 106 regenerates the DRR frames at the new projection angle. The maximally opacified mask image may also be regenerated from the DRR frames using the same specified time window. The updated roadmapping fluoroscopic image 602 resulting from the regenerated opacified mask image may then be displayed. Advantageously, the fluoroscopic image 602 is updated accordingly without exposing the patient to further X-ray radiation or contrast agent. Additionally, efficiency is enhanced by reducing the total procedure time.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The user interface (UI) also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g., enhancing contrast).

The system and processes described in this disclosure are not exclusive. Other systems, processes and devices may be derived in accordance with the principles of the disclosure to accomplish the same objectives. Although this disclosure has been described with reference to particular embodiments, it is to be understood that the embodiments and variations shown and described herein are for illustration purposes only. Modifications to the current design may be implemented by those skilled in the art, without departing from the scope of the disclosure. Further, the processes and applications may, in alternative embodiments, be located on one or more (e.g., distributed) processing devices on a network linking the units of the system. Any of the functions and steps provided in this disclosure may be implemented in hardware, software or a combination of both. No claim element herein is to be construed under the provisions of 35 U.S.C. 112, sixth paragraph, unless the element is expressly recited using the phrase "means for."

Although the disclosure has been described with reference to exemplary embodiments, it is not limited thereto. Those skilled in the art will appreciate that numerous changes and modifications may be made to the preferred embodiments of the disclosure and that such changes and modifications may be made without departing from the true spirit of the disclosure. It is therefore intended that the appended claims cover be construed to all such equivalent variations as fall within the true spirit and scope of the disclosure.

What is claimed is:

1. One or more non-transitory computer-readable media embodying instructions executable by machine to perform operations for angiographic roadmapping comprising:
   projecting a four-dimensional (4D) digital subtraction angiography (DSA) image volume at a predetermined angle to generate a series of two-dimensional (2D) digitally reconstructed radiograph (DRR) images, wherein the 4D DSA image volume is a time-varying three-dimensional (3D) volume with additional flow information about a contrast flow through a vasculature over a time period, wherein the predetermined angle is substantially equal to a projection angle used to acquire a live fluoroscopic image, wherein the series of 2D DRR images show the contrast flow in an image volume within the time period;
   registering the series of 2D DRR images with the live fluoroscopic image;
   generating a maximally opacified image from at least one of the registered 2D DRR images, wherein pixels of the maximally opacified image represent peak contrast levels over a window of time;
   integrating the maximally opacified image with the live fluoroscopic image to generate a roadmapping fluoroscopic image; and
   displaying the roadmapping fluoroscopic image for angiographic roadmapping.

2. The one or more non-transitory computer-readable media of claim 1 including further instructions executable by the machine to regenerate the series of 2D DRR images and the maximally opacified image in the same window of time in response to a change in the projection angle for acquiring the live fluoroscopic image.

3. The one or more non-transitory computer-readable media of claim 1 including further instructions executable by the machine to regenerate the series of 2D DRR images and the maximally opacified image in the same window of time in response to a change in position of a patient.

4. A system for angiographic roadmapping, comprising:
   a non-transitory memory device for storing computer readable program code; and
   a processor in communication with the memory device, the processor being operative with the computer readable program code to perform operations comprising:
      generating one or more two-dimensional (2D) digitally reconstructed radiograph (DRR) images from a four-dimensional (4D) digital subtraction angiography (DSA) image volume, wherein the 4D DSA image volume is a time-varying three-dimensional (3D) volume with additional flow information about a contrast flow through a vasculature over a time period,
      generating a maximally opacified image from at least one of the one or more 2D DRR images, wherein pixels of the maximally opacified image represent peak contrast levels over a window of time,
      integrating the maximally opacified image with a live fluoroscopic image to generate a roadmapping fluoroscopic image, and
      displaying the roadmapping fluoroscopic image for angiographic roadmapping.

5. The system of claim 4 wherein the processor is further operative with the computer readable program code to generate a user interface that is configured to enable a user to specify a beginning time point and an end time point of the window of time.

6. The system of claim 4 wherein the processor is further operative with the computer readable program code to regenerate the one or more 2D DRR images and the maximally opacified image in the same window of time in response to a change in a projection angle used to acquire the live fluoroscopic image.

7. The system of claim 6 wherein the processor is further operative with the computer readable program code to generate a user interface that is configured to enable a user to specify the projection angle.

8. The system of claim 6 wherein the processor is further operative with the computer readable program code to automatically track the projection angle.

9. The system of claim 4 wherein the processor is further operative with the computer readable program code to regenerate the one or more 2D DRR images and the maximally opacified image in the same window of time in response to a change in position of a patient.

10. The system of claim 9 wherein the processor is further operative with the computer readable program code to generate a user interface that is configured to enable a user to specify the position of the patient.

11. The system of claim 9 wherein the processor is further operative with the computer readable program code to automatically track the position of the patient.

12. The system of claim 4 wherein the processor is further operative with the computer readable program code to perform 4D reconstruction of time-varying image data to generate the 4D DSA image volume.

13. The system of claim 4 wherein the processor is further operative with the computer readable program code to generate the one or more 2D DRR images by projecting the 4D DSA image volume at a predetermined angle.

14. The system of claim 13 wherein the predetermined angle comprises a projection angle used to acquire the live fluoroscopic image.

15. The system of claim 4 wherein the processor is further operative with the computer readable program code to generate the one or more 2D DRR images by generating a series of 2D DRR images that show contrast flow in a same volume within a time period.

16. The system of claim 4 wherein the processor is further operative with the computer readable program code to register the one or more 2D DRR images with the live fluoroscopic image.

17. The system of claim 4 wherein the processor is further operative with the computer readable program code to generate the maximally opacified image by processing the one or more 2D DRR images pixel by pixel to determine the peak contrast level at each pixel location over the window of time.

18. The system of claim 4 wherein the processor is further operative with the computer readable program code to integrate the maximally opacified image with the live fluoroscopic image by subtracting the maximally opacified image from the live fluoroscopic image.

19. A method of angiographic roadmapping, comprising:

generating one or more two-dimensional (2D) digitally reconstructed radiograph (DRR) images from a four-dimensional (4D) digital subtraction angiography (DSA) image volume, wherein the 4D DSA image volume is a time-varying three-dimensional (3D) volume with additional flow information about a contrast flow through a vasculature over a time period;

generating a maximally opacified image from at least one of the one or more 2D DRR images, wherein pixels of the maximally opacified image represent peak contrast levels over a window of time;

integrating the maximally opacified image with a live fluoroscopic image to generate a roadmapping fluoroscopic image; and displaying the roadmapping fluoroscopic image for angiographic roadmapping.

20. The method of claim 19 further comprises generating a user interface that is configured to enable a user to specify a beginning time point and an end time point of the window of time.

21. The one or more non-transitory computer-readable media of claim 1 wherein each doxel of the 4D DSA image volume represents the contrast flow in the vasculature at a particular three-dimensional location and at a particular time.

* * * * *